United States Patent [19]

Zanno et al.

[11] Patent Number: 4,619,782

[45] Date of Patent: Oct. 28, 1986

[54] L-AMINODICARBOXYLIC ACID GEM-DIAMINES

[75] Inventors: Paul R. Zanno, Nanuet; Ronald E. Barnett, Suffern; Glenn M. Roy, Garnerville, all of N.Y.

[73] Assignee: General Foods Corporation, White Plains, N.Y.

[21] Appl. No.: 723,599

[22] Filed: Apr. 15, 1985

[51] Int. Cl.$^4$ ............................................. C07K 5/06
[52] U.S. Cl. ................... 560/122; 560/117; 560/119; 560/116; 560/124; 560/123
[58] Field of Search ................................ 260/112.5 K

[56] References Cited

FOREIGN PATENT DOCUMENTS

0128654A2 12/1984 European Pat. Off. .

OTHER PUBLICATIONS

Miyoshi et al, *Bulletin of Chemical Society of Japan*, 51, 1433–1440 (1978).

Tsang et al., *J. Med. Chem.*, 27, No. 12, 1663–1668 (1984).

Ariyoshi et al., *Bulletin of the Chemical Society of Japan*, 72(2), 326–330 (1974).

*Primary Examiner*—Delbert R. Phillips
*Assistant Examiner*—F. T. Moezie
*Attorney, Agent, or Firm*—Linn I. Grim; Thomas A. Marcoux; Daniel J. Donovan

[57] ABSTRACT

Sweeteners of the formula:

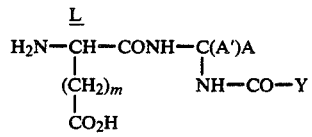

and food-acceptable salts thereof, where the substituents are disclosed herein.

42 Claims, No Drawings

L-AMINODICARBOXYLIC ACID GEM-DIAMINES

FIELD OF THE INVENTION

This invention relates to a novel group of compounds and more particularly to a novel group of compounds particularly well suited as sweeteners in edible foodstuff.

DESCRIPTION OF THE PRIOR ART

Sweetness is one of the primary taste cravings of both animals and humans. Thus, the utilization of sweetening agents in foods in order to satisfy this sensory desire is well established.

Naturally occuring carbohydrate sweeteners such as sucrose, are still the most widely used sweetening agents. While thse naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. patents which disclose sweetener mixtures include for example, U.S. Pat, Nos. 4,228,198; 4,158,068; 4,154,862; and 3,717,477

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener for most sweetener applications. Furthermore, the sweeteners sought must have good temporal and sensory qualities. Sweeteners with good temporal qualities produce a time-intensity sweetness response similar to natural sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S Pat. No. 4,448,716 metal complex salts of dipeptide sweeteners are disclosed. In the background of this patent a generic formula is described as an attempt to represent dipeptide sweeteners disclosed in four prior patents: U.S. Pat. Nos. 3,475,403; 3,492,131; Republic of South Africa Pat. No. 695,083 published July 10, 1969; Republic of South Africa Pat. No. 695,910 published Aug. 14, 1969. The general formula attempting to represent these patents is as follows:

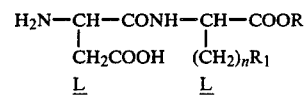

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $(S(O)_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartylmethionine methyl esters are disclosed by Brussel, Peer and Van der Heijden in *Chemical Senses and Flavour*, 4, 141–152 (1979) and in *Z Lebensm. Untersuch-Forsch.*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cys(t-But)-OMe
α-L-Asp-L-Met-OMe

In U.S. Pat. No. 4,399,163 to Brennan et al., sweeteners having the following formulas are disclosed:

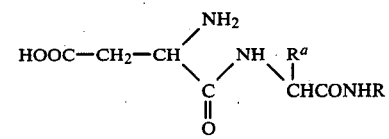

and physiologically acceptable cationic and acid addition salts thereof wherein
 $R^a$ is $CH_2OH$ or $CH_2OCH_3$;
 R is a branched member selected from the group consisting of fenchyl, diisopropylcarbinyl, d-methyl-t-butylcarbinyl, d-ethyl-t-butyl-carbinyl, 2-methylthio-2,4-dimethylpentan-3-yl, di-t-butyl-carbinyl,

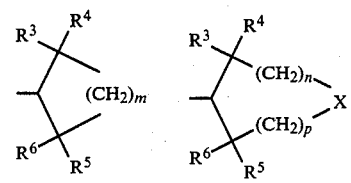

-continued

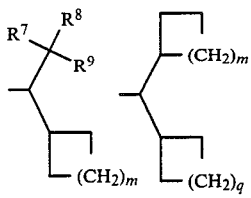

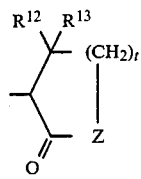

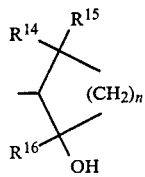

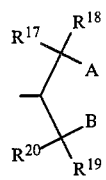

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninoamides or L-aspartyl-D-serinamides.

European Patent Application No. 95772 to Tsau describe aspartyl dipeptide sweeteners of the formula:

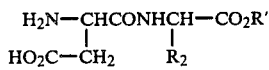

wherein R' is alkyl of 1 to 6 carbons, and $R_2$ is phenyl, phenylakylenyl or cyclohexylalkenyl, wherein the alkenyl group has 1 to 5 carbons. Closely related is U.S. Pat. No. 4,439,460 to Tsau, et al. which describes dipeptide sweeteners of the formula:

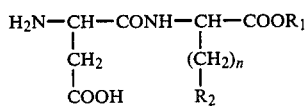

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al., $R_2$ is defined as cycloalkenyl or phenyl. U.S. Pat. No. 3,695,898 to Hill defines $R_2$ as a monoor a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkdienyl, or $S(O)_m$ lower alkyl provided that n is 1 or 2 and m is 0 or 2. Closely related are U.S. Pat. Nos. 4,448,716, 4,153,737, 4,031,258, 3,962,468, 3,714,139, 3,642,491, and 3,795,746.

U.S. Pat. No. 3,803,223 to Mazur, et al. describe dipeptide sweeteners and anti-inflammatory agents having the formula:

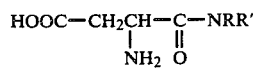

wherein R is hydrogen or a methyl radical and R' is a radical selected from the group consisting of alkyl, or

wherein Alk is a lower alkylene radical, X is hydrogen or hydroxy, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

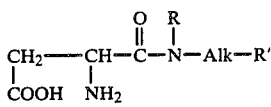

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

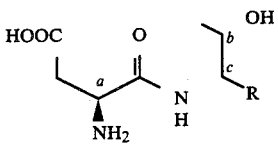

wherein R is $C_4$-$C_9$ straight, branched or cyclid alkyl, and wherein carbons a, b and c have the (S) configuration.

European Patent Application 48,051 describes dipeptide sweeteners of the formula:

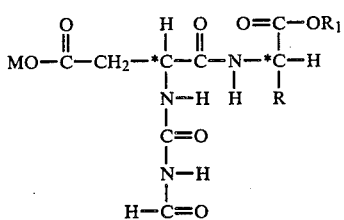

wherein M represents hydrogen, ammonium, alkali or alkaline earth,

R represents

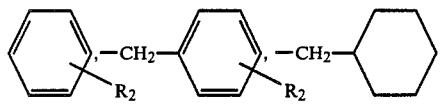

$R_1$ represents methyl, ethyl, propyl,
$R_2$ represents -OH, or OCH$_3$,
* signifies an L-optical configuration for this atom.

German Patent Application No. 7259426 discloses L-aspartyl-3-fenchylalanine methyl ester as a sweetening agent.

U.S. Pat. No. 3,971,822 to Chibata, et al., disclose sweeteners having the formula:

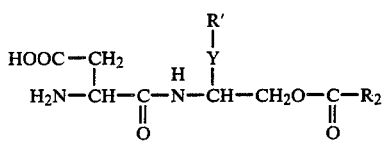

wherein R' is hydrogen or hydroxy, $R_2$ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S Pat. No. 3,907,366 to Fujino, et al. discloses L-aspartyl-aminomalonic acid alkyl fenchyl diester and its physiologically acceptable salts as useful sweeteners. U.S. Pat. No. 3,959,245 disclose the 2-methyl cyclohexyl analog of the abovementioned patent.

U.S. Pat. No. 3,920,626 discloses N-αL-aspartyl derivatives of lower alkyl esters of O-lower-alkanoyl-L-serine, β-alanine, γ-aminobutyric acid and D-β-aminobutyric acid as sweeteners.

Miyoshi, et al. in *Bulletin of Chemical Society of Japan*, 51, p. 1433-1440 (1978) disclose compounds of the following formula as sweeteners:

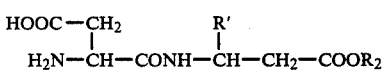

wherein R' is H, CH$_3$, CO$_2$CH$_3$, or benzyl and $R_2$ is lower alkyl or unsubstituted or substituted cycloalkyl.

European Patent Application No. 128,654 describes gem-diaminoalkane sweeteners of the formula:

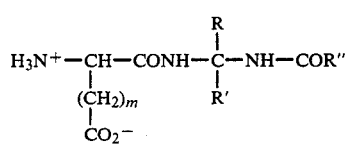

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physically acceptable salts thereof.

U.S. Pat. No. 3,801,563 to Nakajima, et al. disclose sweeteners of the formula:

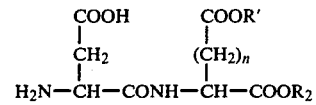

wherein R' is a branched or cyclic alkyl group of 3 to 8 carbon atoms, $R_2$ is a lower alkyl group of 1 to 2 carbon atoms and n is a integer of 0 or 1.

European Patent Application No. 34,876 describes amides of L-aspartyl-D-amino acid dipeptides of the formula:

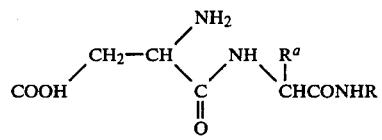

wherein $R^a$ is methyl, ethyl, n-propyl or isopropyl and R is a branched aliphatic, alicyclic or heterocyclic member which is branched at the alpha carbon atom and also branched again at one or both of the beta carbon atoms. These compounds are indicated to be of signficant sweetness.

In the *Journal of Medicinal Chemistry*, 1984, Vol. 27, No. 12, pp. 1663-8, are described various sweetener dipeptide esters, including L-aspartyl-α-aminocycloalkane methyl esters.

The various dipeptide esters of the prior art have been characterized as lacking significant stability at low pH values and/or thermal stability. These characterstics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are amides of certain α-aminodicarboxylic acids and gem-diamines which are low calorie sweeteners that possess a high order of sweetness with pleasing taste and higher stability at acid pH and elevated temperatures compared to known dipeptide sweeteners.

This invention provides new sweetening compounds represented by the formula:

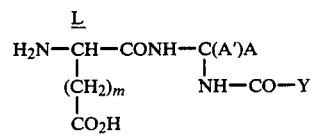

wherein
A is H, Co$_2$R where R is alkyl containing 1-3 carbon atoms,
A' is hydrogen or alkyl containing 1-3 carbon atoms provided that when A=H, A' must be H.
A and A' taken together with the carbon atom to which they are attached form cycloalkyl containing 3-4 carbon atoms;
Y is —(CHR$_2$)$_n$—R$_1$ or —CHR$_3$R$_4$;

$R_1$ is cycloalkyl, cycloalkenyl, lower alkyl substituted cycloalkyl or cycloalkenyl, bicycloalkyl, bicycloalkenyl or tricycloalkyl containing up to 10 ring carbon atoms and up to a total of 12 carbon atoms;

$R_2$ is H or alkyl containing 1—4 carbon atoms;

$R_3$ and $R_4$ are each cycloalkyl containing 3-4 ring carbon atoms;

$n=0$ or 1; and $m=0$ or 1;

and food-acceptable salts thereof.

DESCRIPTION OF THE PREFERRED EMBODIMENTS

In accordance with the present invention, the preferred compounds are those in which $R_1$ is an alkyl-substituted cycloalkyl or bicycloalkyl containing 5–7 ring carbon atoms and up to a total of 10 carbon atoms. Especially preferred are cycloalkyl substituted with at least one methyl group on the $\beta$ and/or $\beta'$ carbon atoms of the cycloalkyl ring. Particularly preferred cycloalkyls include cyclopropyl, cyclopentyl, and cyclohexyl and the preferred bicycloalkyl is fenchyl.

Also preferred are those compounds in which $n=0$. In those compounds in which $n=1$, $R_1$ is preferably a cyclopropyl group and $R_2$ is preferably tertiary butyl, isopropyl or cyclopropyl.

The groups representative of Y in the present new compounds include such groups as cycloalkyl, e.g., cyclobutyl, cyclopentyl, cyclohexyl, cycloheptyl, etc.; alkyl-substituted cycloalkyls, e.g., 1-methylcyclopentyl, 1-methylcyclohexyl, 1-methylcyclobutyl, 1-methylcycloheptyl, 1-ethylcyclobutyl, 1-ethylcyclopentyl, 1-ethylcycloheptyl, 1-ethylcyclohexyl, 1-isopropylcyclobutyl, 1-isopropylcyclopentyl, 1-isopropylcyclohexyl, 1-isopropylcycloheptyl, 1,2-dimethylcyclohexyl, 1,2-dimethylcyclopentyl, 1,2-dimethylcycloheptyl, 1,3-dimethylcyclohexyl, 1,3-dimethylcyclopentyl, 1,3-dimethylcycloheptyl, 1,4-dimethylcyclohexyl, 1,4-dimethylcycloheptyl, 2,3-dimethylcyclopentyl, 2,3-dimethylcyclohexyl, 2,3-dimethylcycloheptyl, 2,4-dimethylcyclopentyl, 2,4-dimethylcyclohexyl, 2,4-dimethylcycloheptyl, 2,5-dimethylcyclopentyl, 2,5-dimethylcyclohexyl, 2,5-dimethylcycloheptyl, 2,6-dimethylcyclohexyl, 2,6-dimethylcycloheptyl, 2,7-dimethylcycloheptyl, 3,4-dimethylcyclopentyl, 3,4-dimethylcyclohexyl, 3,4-dimethylcycloheptyl, 3,5-dimethylcyclopentyl, 3,5-dimethylcyclohexyl, 3,5-dimethylcycloheptyl, 4,5-dimethylcyclopentyl, 4,5-dimethylcyclohexyl, 4,5-dimethylcycloheptyl, 3,6-dimethylcyclohexyl, 3,6-dimethylcycloheptyl, 3,7-dimethylcycloheptyl, 4,6-dimethylcycloheptyl, 4,6-dimethylcyclohexyl, 4,7-dimethylcycloheptyl, 5,6-dimethylcyclohexyl, 5,6-dimethylcyclohexyl, 5,6-dimethylcycloheptyl, 5,7-dimethylcycloheptyl, 6,7-dimethylcycloheptyl, 2,2-dimethylcyclopentyl, 2,2-dimethylcyclohexyl, 2,2-dimethylcycloheptyl, 3,3-dimethylcyclopentyl, 3,3-dimethylcyclohexyl, 3,3-dimethylcycloheptyl, 4,4-dimethylcyclohexyl, 4,4-dimethylcycloheptyl, 2,2,3-trimethylcyclopentyl, 2,2,3-trimethylcyclohexyl, 2,2,3-trimethylcycloheptyl, 2,2,4-trimethylcyclopentyl, 2,2,4-trimethylcyclohexyl, 2,2,4-trimethylcycloheptyl, 2,2,5-trimethylcyclopentyl, 2,2,5-trimethylcyclohexyl, 2,2,5-trimethylcycloheptyl, 2,2,6-trimethylcyclohexyl, 2,2,6-trimethylcyclohepty 2,2,7-trimethylcycloheptyl, 1,2,2-trimethylcyclopentyl, 1,2,2-trimethylcyclohexyl, 1,2,2-trimethylcycloheptyl, 1,3,3-trimethylcyclopentyl, 1,3,3-trimethylcyclohexyl, 1,3,3-trimethylcycloheptyl, 1,4,4-trimethylcyclohexyl, 1,4,4-trimethylcyclopentyl, 3,3,4-trimethylcyclopentyl, 3,3,4-trimethylcyclohexyl, 3,3,4-trimethylcycloheptyl, 2,3,3-trimethylcyclopentyl, 2,3,3-trimethylcyclohexyl, 2,3,3-trimethylcycloheptyl, 2,4,4-trimethylcyclopentyl, 2,4,4-trimethylcyclohexyl, 2,4,4-trimethylcycloheptyl, 1,2,3-trimethylcyclopentyl, 1,2,3-trimethylcyclohexyl, 1,2,3-trimethylcycloheptyl, 1,2,4-trimethylcyclopentyl, 1,2,4-trimethylcyclohexyl, 1,2,4-trimethylcycloheptyl, 1,2,5-trimethylcyclopentyl, 1,2,5-trimethylcyclohexyl, 1,2,5-trimethylcycloheptyl, 1,2,6-trimethylcyclohexyl, 1,2,6-trimethylcycloheptyl, 1,2,7-trimethylcycloheptyl, 2,3,4-trimethylcyclopentyl, 2,3,4-trimethylcyclohexyl, 2,3,4-trimethylcycloheptyl, 2,3,5-trimethylcyclopentyl, 2,3,5-trimethylcyclohexyl, 2,3,5-trimethylcycloheptyl, 2,3,6-trimethylcyclohexyl, 2,3,6-trimethylcycloheptyl, 2,3,7-trimethylcycloheptyl, 3,4,4-trimethylcyclohexyl, 3,4,4-trimethylcyclopentyl, 2,2,5,5-tetramethylcyclopentyl, 2,2,5,5-tetramethylcyclohexyl, 2,2,5,5-tetramethylcycloheptyl, 2,2,6,6-tetramethylcyclohexyl, 2,2,6,6-tetramethylcycloheptyl, 2,2,7,7-tetramethylcycloheptyl, 2,2,4,4-tetramethylcyclopentyl, 2,2,4,4-tetramethylcyclohexyl, 2,2,4,4-tetramethylcycloheptyl, 2,2,3,3-tetramethylcyclopentyl, 2,2,3,3-tetramethylcyclohexyl, 2,2,3,3-tetramethylcycloheptyl, 3,3,4,4-tetramethylcyclopentyl, 3,3,4,4-tetramethylcyclohexyl, 3,3,4,4-tetramethylcycloheptyl, 3,3,5,5-tetramethylcyclohexyl, 3,3,5,5-tetramethylcycloheptyl, 1,2,3,4-tetramethylcyclopentyl, 1,2,3,4-tetramethylcyclohexyl, 1,2,3,4-tetramethylcycloheptyl, 1,2,3,5-tetramethylcyclopentyl, 1,2,3,5-tetramethylcyclohexyl, 1,2,3,5-tetramethylcycloheptyl, 1,2,3,6-tetramethylcyclohexyl, 1,2,3,6-tetramethylcycloheptyl, 2,3,4,5-tetramethylcyclopentyl, 2,3,4,5-tetramethylcyclohexyl, 2,3,4,5-tetramethylcycloheptyl, 2,3,4,6-tetramethylcycloheptyl, 2,3,4,6-tetramethylcyclohexyl, 2,3,4,7-tetramethylcycloheptyl, 2,2,3,4-tetramethylcyclopentyl, 2,2,3,4-tetramethylcyclohexyl, 2,2,3,4-tetramethylcycloheptyl, 2,2,3,5-tetramethylcyclopentyl, 2,2,3,5-tetramethylcyclohexyl, 2,2,3,5-tetramethylcycloheptyl, 2,2,3,6-tetramethylcyclohexyl, 2,2,3,6-tetramethylcycloheptyl, 2,2,3,7-tetramethylcycloheptyl, 3,3,3,4-tetramethylcyclohexyl, 2.3,3,4-tetramethylcyclopentyl, 2,3,3,4-tetramethylcycloheptyl, 2,3,3,5-tetramethylcyclopentyl, 2,2,3,5-tetramethylcyclohexyl, 2,3,3,5-tetramethylcycloheptyl, 2,3,3,6-tetramethylcyclohexyl, 2,3,3,6-tetramethylcycloheptyl, 2,3,3,7-tetramethylcycloheptyl, 2,2,3,4-tetramethylcyclopentyl, 2,2,3,4-tetramethtlcyclohexyl, 2,3,3,4-tetramethylcycloheptyl, 2,2,3,5-tetramethylcyclopentyl, 2,2,3,5-tetramethylcyclohexyl, 2,2,3,6-tetramethylcyclohexyl, 2,2,3,6-tetramethylcycloheptyl, 2,2,3,7-tetramethylcycloheptyl, 2,2,4,5-tetramethylcyclopentyl, 2,2,4,5-tetramethylcyclohexyl, 2,2,4,5-tetramethylcycloheptyl, 2,2,4,6-tetramethylcyclohexyl, 2,2,4,6-tetramethylcycloheptyl, 2,2,4,7-tetramethylcycloheptyl, dicyclopropylmethyl, t-butylcyclopropylmethyl, t-butylcyclopentylmethyl, 2-isopropylcyclopentyl, 2-t-butylcyclopentyl, 2-isopropylcyclohexyl, 2-t-butylcyclopentyl, 2-isopropylcyclohexyl, 2-t-butylcyclohexyl, 2-t-amylcyclopentyl, t-amylcyclopropylmethyl, dicyclobutylmethyl, t-butylcyclobutylmethyl, 3-methylcycloheptylisopropyl, 2-methylcycloheptylisopropyl, 2-methycyclohexylisopropyl, 2-methylcyclopentylisopropyl, etc.; cycloalkenes, e.g., cyclopentenyl, cyclohexenyl, cycloheptenyl, etc.; alkyl-substituted cycloalkenes, e.g., 1-methyl-3-cyclopentenyl, 1-methyl-3-cyclohexenyl 1-methyl-3-cycloheptenyl, 1-methyl-4-cycloheptenyl, 3-cyclopentenylisopropyl, 3-cyclohexenylisopropyl, 3-cycloheptenylisopropyl, 4-cycloheptenylisopropyl, 3-cyclopentenylmethyl, 3-cyclopentenylethyl, 3-cyclohexenylpropyl, 3-cyclohexenylethyl, 3-cycloheptenylpropyl, 3-cycloheptenylethyl, 4-cycloheptenylmethyl, 4-cycloheptenylethyl, 2-methyl-3-cyclohexenyl, 2-methyl-3-cyclopentenyl, 2-methyl-3-cycloheptenyl, 2-methyl-4-cycloheptenyl, 3-methyl-3-cyclohexenyl, 3-methyl-3-cyclopentenyl, 3-methyl-3-cycloheptenyl, 4-methyl-3-cycloheptenyl, 4-methyl-3-cyclohexenyl, 4-methyl-3-cyclopentenyl, 5-methyl-3-cyclopentenyl, 5-methyl-3-cyclohexenyl, 5-methyl-3-cycloheptenyl, 6-methyl-3-cyclohexenyl, 6-methyl-3-cycloheptenyl, 2-methyl-2-cyclopentenyl, 2-methyl-2-cyclohexenyl, 2-methyl-2-cycloheptenyl, 2-methyl-2-cyclopentenyl, 3-methyl-2-cyclohexenyl, 3-methyl-2-cycloheptenyl, 1-methyl-2-cyclopentenyl, 1-methyl-2-cyclohexenyl, 1-methyl-2-cycloheptenyl, 5-methyl-2-cyclopentenyl, 4-methyl-2-cyclopentenyl, 4-methyl-2-cycloheptenyl, 5-methyl-2-cyclohexenyl, 5-methyl-2-cycloheptenyl, 6-methyl-2-cyclohexenyl, 6-methyl-2-cycloheptenyl, 7-methyl-2-cycloheptenyl, 2,3-dimethyl-2-cyclopentenyl, 2,3-dimethyl-2-cyclohexenyl, 2,4-dimethyl-2-cyclopentenyl, 2,4-dimethyl-2-cyclohexenyl, 2,5-dimethyl-2-cyclohexenyl, 2,5-dimethyl-2-cyclopeptenyl, 2,6-dimethyl-2-cyclohexenyl, 2,6-dimethyl-3-cyclohexenyl, 2,5-dimethyl-3-cyclohexenyl, 2,5-dimethyl-2-cyclopentenyl, 2,4-dimethyl-3-cyclopentenyl, 2,4-dimethyl-3-cyclohexenyl, 3,3-dimethyl-3-cyclopentenyl, 3,3-dimethyl-3-cyclohexenyl, 3,4-dimethyl-3-cyclopentenyl, 3,4-dimethyl-3-cyclohexenyl, 4,5-dimethylcyclo-3-pentenyl, 4,5-dimethyl-cyclo-3-hexenyl, 5,5-dimethyl-3-cyclohexenyl, 5,5-dimethyl-3-cyclopentenyl, 5,5-dimethyl-3-cycloheptenyl, 6,6-dimethyl-3-cyclohexenyl, 1,2-dimethyl-3-cyclopentenyl, 1,2-dimethyl-3-cyclohexenyl, 1,3-dimethyl-3-cyclopentenyl, 1,3-dimethyl-3-cyclohexenyl, 1,3-dimethyl-3-cycloheptenyl, 1,4-dimethyl-3-cyclopentenyl, 1,4-dimethyl-3-cyclohexenyl, 1,4-dimethyl-3-cyclohexenyl, 1,5-dimethyl-3-cyclopentenyl, 1,5-dimethyl-3-cyclohexenyl, 1,5-dimethyl-3-cycloheptenyl, 2,2,6-trimethyl-3-cyclohexenyl, 2,2,5-trimethyl-3-cyclohexenyl, 2,5,5-trimethyl-3-cyclohexenyl, 2,5,5-trimethyl-3-cyclopentenyl, 2,7,7-trimethyl-3-cycloheptenyl, 2,7,7-trimethyl-4-cycloheptenyl, 2,2,7-trimethyl-3-cycloheptenyl, 2,2,7-trimethyl-4-cycloheptenyl, 2,3,6-trimethyl-3-cyclohexenyl, 2,3,7-trimethyl-3-cycloheptenyl, 2,3,5-trimethyl-3-cyclopentenyl, 2,2,6,6-tetramethyl-3-cyclohexenyl, 2,2,5,5-tetramethyl-3-cyclopentenyl, 2,2,7,7-tetramethyl-3-cycloheptenyl, 2,3,5,5-tetramethyl-3-cyclopentenyl, 2,3,6,6-tetramethyl-3-cyclohexenyl, 2,3,7,7-tetramethyl-3-cycloheptenyl, 2,3,6,6-tetramethyl-3-cycloheptenyl, 2,3,5,5-tetramethyl-3-cyclohexenyl, 2,3,4,5-tetramethyl-3-cyclopentenyl, 2,3,4,5-tetramethyl-3-cyclohexenyl, etc.; bicyclic compounds, such as norbornyl, norcaranyl, norpinanyl, bicyclo [2.2.2] octyl, etc.; alkyl substituted bicyclic compounds, e.g., 6,6-dimethyl-bicyclo [3.1.1] heptyl, 6,7,7-trimethylnorbornyl (bornyl or camphanyl), pinanyl, thujanyl, caranyl, fenchyl, 2-norbornylmethyl, etc.; unsubstituted and alkyl-substituted bicycloalkenes such as norbornenyl, norpinenyl, norcarenyl, 2-(4-norbornenyl)methyl, pinenyl, carenyl, fenchenyl, etc.; and tricyclo compounds such as adamantyl and alkyl-substituted adamantyl, etc.

The preferred $R_1$ is cycloalkyl or bicycloalkyl or alkyl-substituted cycloalkyl or bicycloalkyl, especially where the alkyl group is in the $\beta$ or $\beta'$ positions. Further, preference exists for compounds in which $R_1$ is a cycloalkyl with two, three or four alkyl groups in the $\beta$, $\beta'$ positions such as $\beta$, $\beta$, $\beta'$, $\beta'$-tetraalkyl-substituted cyclobutyl, cyclopropyl, cyclohexyl, cyclopentyl, and cycloheptyl, as well as $\beta$, $\beta$, $\beta'$-trialkyl substituted cyclobutyl, cyclopropyl, cyclohexyl, cyclopentyl, and cycloheptyl, and fenchyl. Also preferred $\beta$-alkylcycloalkyls in which the alkyl group is isopropyl or tertiary butyl.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, metahydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention, several reaction schemes may be employed. In one reaction scheme, compounds of general formula II (protected α-aminodicarboxylic acid) and III (gem-diamine) are condensed to form compounds of general

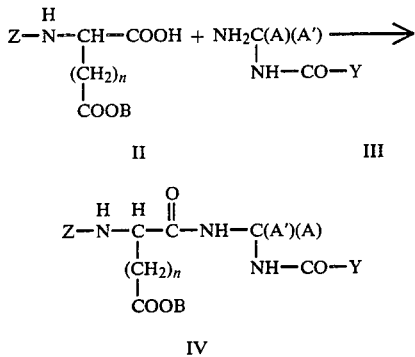

In these, group Z is an amino protecting group, B is a carboxyl protecting group, and A, A', Y, and n have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzylcarbonyl for A and benzyl for B.

Coupling of compounds with general formula II to compounds having general formula III employs established techniques in peptide chemistry. One such technique uses dicyclohexylcarbodiimide (DCC) as the coupling agent. The DCC method may be employed with or without additives such as 4-dimethylaminopyridine or copper (II). The DCC coupling reaction generally proceeds at room temperature, however, it may be carried out from about $-20°$ to $50°$ C. in a variety of solvents inert to the reactants. Thus, suitable solvents include, but are not limited to, N,N-dimethyl-formamide, methylene chloride, toluene and the like. Preferably, the reaction is carried out under an inert atmosphere such as argon or nitrogen. Coupling usually is complete within 2 hours but may take as long as 24 hours depending on reactants.

Various other methods can be employed to prepare the desired compounds. The following illustrates such methods using aspartic acid as the amino dicarboxylic acid.

For example, U.S. Pat. Nos. 3,786,039, 3,833,552, 3,879,372 and 3,933,781 disclose the reaction of N-protected aspartic anhydrides with amino acids and amino acid derivatives to yield the desired products. These N-protected aspartic anhydrides can be reacted with compounds of formula III by methods disclosed in the above patents. As described in U.S. Pat. No. 3,786,039 compounds of formula III can be reacted directly in inert organic solvents with L-aspartic anhydride having its amino group protected by a formyl, carbobenzloxy, or p-methoxycarbobenzloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at $0°$ to $60°$ C. in an inert solvent. The N-acyl-L-aspartic anhydrides are reacted with preferably 1 to 2 moles of compounds of formula III in an organic solvent capable of dissolving both and inert to the same. Suitable solvents are, but not limited to, ethyl acetate, methyl propionate, tetrahydrofuran, dioxane, ethyl ether, N,N-dimethylformamide and benzene. The reaction proceeds smoothly at $0°$ to $30°$ C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of $-10°$ to $50°$ C. and at a pH of 4–12.

Another method for the synthesis of the desired compounds is the reaction of compounds of formula III with suitable aspartic acid derivatives in which protecting groups have been attached to the amino and beta-carboxy groups and the alpha carboxy group has been converted to a reactive ester function. As disclosed in U.S. Pat. No. 3,475,403 these coupled products may be deprotected as described to yield the desired compounds of formula I.

An alternative scheme to the desired coupled compounds involves reaction of compounds of formula III with L-aspartic acid N-thiocarboxyanhydride by the method of Vinick and Jung, Tet. Lett., 23, 1315–18 (1982). An additional coupling method is described by T. Miyazawa, Tet. Lett., 25, 771 (1984).

Compounds of formula III can be synthesized using art-recognized techniques from commercially available starting materials. Compounds of formula III can be prepared from compounds of formula V

By utilizing techniques known in the art, such as the Hoffman rearrangement, the Lossen rearrangement, Curtius rearrangement, or Schmidt rearrangement, compounds of formula V can be transformed into compounds of formula III. The reaction is carried out in the presence of base, such as sodium hydroxide or iodobenzene bis(trifluoroacetate). Reaction temperatures are in the range of $-78°$ C. to reflux. The reaction is carried out in a solvent that will dissolve both reactants and is inert to both as well. Suitable solvents include methylene chloride, diethyl ether, tetrahydrofuran, dimethylsulfoxide, N,N-dimethylformamide and the like.

Compound V can be prepared by art-recognized procedures. For example, it may be prepared by first treating an amino acid derivative of formula VI

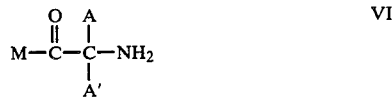

wherein A and A' have the aforementioned meanings and M is a carboxy protecting group, with the appropriate acid derivatives, such as acid chloride. The amino acid derivative VI may be a free amino acid or may be carboxyl protected. A preferred carboxyl-protecting group is the trialkylsilylester group, such as trimethylsilyl group. The newly formed amide is then deprotected and then transformed to V by reacting with ammonia according to well established procedures. Compounds of formula IV can also be prepared from the reaction of a monoacetylated gem diaminoalkane or its salts (VII) with an acid derivative, (VIII), e.g., an acid chloride:

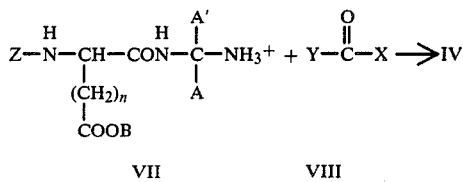

In these groups, Z, B, A, A', Y and n have the same meaning as previously described and X is hydroxy, halide, or alkoxy. This reaction is carried out under basic conditions. This reaction may be carried out in a variety of solvents that will dissolve both reactants and is inert to both as well. Suitable solvents include acetonitrile, methylene chloride, diethyl ether, N,N-dimethylformamide, tetrahydrofuran, dioxane and the like. Compounds of general formula VII are synthesized using art-recognized techniques. For example, compounds of formula IX

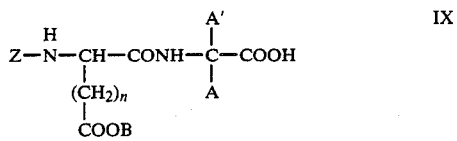

are transferred into compounds of formula VII by one of several standard methods, such as the Curtius rearrangement or the Schmidt rearrangement. Alterntively, the carboxylic acid derivative may first be transformed to the amide (X)

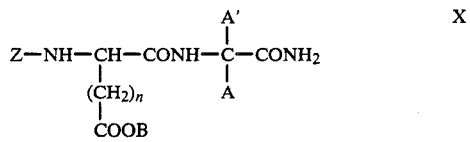

by condensation with ammonia. In a preferred method, the dipeptide IX is activated via the mixed carboxyliccarbonic anhydride at low temperature and condensed with the ammonia salt of 1-hydroxybenzotriazole. The amide may then be transformed to the gem-diamino alkane or its salt (VII) via the Hofmann rearrangement using sodium hypobromite. Alternatively, a preferred reagent for effecting this transformation is iodobenzene bis(trifluoroacetate), as described above. Compounds of formula IX are formed by the reaction of a protected dicarboxylic acid (XI) with the appropriate amino acid (XII) under amide-forming conditions well-known in the art:

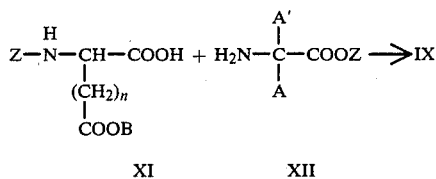

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained from the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium, potassium, lithium, or the alkaline earth metal salts such as calcium or magnesium, as well as aluminum, zinc and like salts.

Conversion of the free peptide derivatives of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

The compounds of the present invention have one asymmetric site, which is designated by an asterik (*) in the formula below, and one pseudoasymmetric sites which is designated by a double asterik (**):

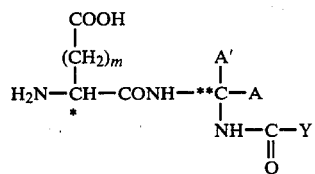

Whenever A is identical to A' the compounds of the present invention have only one asymmetric site, designated by the asterik, in the dicarboxylic acid moiety. Although both the D and L forms are possible the preferred compounds are those in which the dicarboxylic acid group is in the L-configuration. Whenever, the groups A' and A are different, the carbon atoms designated by the double asterik becomes an asymmetric center and the compounds of the present invention will contain at least two asymmetric centers. Regardless, the configuration around each of the asymmetric sites, whenever present, may exist in either the D or L forms, and all possible stereoisomers are contemplated to be within the scope of the present invention. Since the aspartyl group is in the L-configuration, whenever an asymmetric center is present at the other carbon site, the compounds of the present invention are diastereomers, which can be separated, if desired, by art-recognized techniques, as, for example, by chromatography. However, mixtures of at least any two stereoisomers exhibit sweetness properties and are useful as sweeteners.

The following examples further illustrate the invention.

EXAMPLE 1

N-L-Aspartyl-N'-(2,2,5,5-tetramethylcyclopentylcarbonyl)-2,2-diamino acetic acid methyl ester A. 2-Amino-malonic acid monomethyl ester is dissolved in dimethylformamide (400 ml), and treated with chlorotrimethylsilane and the mixture is stirred at room temperature until a homogeneous solution is obtained. Meanwhile, N-α-benzyloxycarbonyl-α-benzyl-L-aspartic acid is dissolved in a 1:1 mixture of dimethylformamide and tetrahydrofuran (880 ml), cooled to $-15°$ C. and treated with N-methylmorpholine and isobutyl chloroformate. After 8 minutes' activation at $-15°$ C. the precooled solution of the newly formed silyl ester from above is added, followed by the dropwise addition of N-methylmorpholine, ensuring that the temperature of the reaction mixture is maintained at $-15°$ C. The solution is allowed to warm to room temperature slowly and is stirred for several hours before acidifying to pH 1-2 (with cooling) using aqueous hydrochloric acid. Chloroform is added, the phases separated and the aqueous layer re-extracted with chloroform. The combined organic extracts are washed with 1N hydrochloric acid (3 x), saturated aqueous sodium chloride and dried (MgSO$_4$) After evaporation of the solvent under reduced pressure, the oily residue is triturated with ether. The resulting solid is filtered and dried in vacuo.

B. The product from Part A is dissolved in dimethylformamide (600 ml), cooled to $-15°$ C. and treated with N-methylmorpholine and isobutyl chloroformate. After 5 minutes' activation at $-15°$ C., 1-hydroxybenzotriazole ammonium salt is added as a solid, and the mixture is stirred at $-15°$ C. for 15 minutes. After warming slowly to room temperature over 4 hours, chloroform and water are added, the phases are separated and the aqueous phase is re-extracted with chloroform. The combined organic extracts are washed with 1N hydrochloric acid (3 x), saturated aqueous sodium bicarbonate (3 x), saturated sodium chloride and dried (MgSO$_4$). The solvent is evaporated under reduced pressure and the solid residue recrystallized from ethyl acetate/hexanes.

C. The product from Part B is dissolved in acetonitrile (50 ml) and the solution is diluted with an equal volume of water. Iodobenzene bis(trifluoroacetate) is then added and the reaction mixture is stirred at room temperature for 4 hours (clear solution after approximately 2 hours). The solution is evaporated and the residue redissolved in aqueous HCl and lyophilized.

D. The product from Part C is dissolved in tetrahydrofuran (50 ml) 2,2,5,5-Tetramethylcyclopentanecarbonyl chloride (prepared from the reaction of 2,2,5,5-tetramethyl-1-carboxycyclopentane and thionyl chloride) followed by potassium bicarbonate and water, and the mixture is stirred at room temperature. After 4.0 hours, ethyl acetate and water are added, the phases separated and the aqueous phase is extracted with ethyl acetate. The combined organic phases are washed with 1M sodium bicarbonate (2 x), 2N hydrochloric acid (3 x), again with 1M sodium bicarbonate (2 x) and finally with saturated sodium chloride and dried (MgSO$_4$). The solution is filtered, evaporated under reduced pressure and the residue is triturated with ether.

E. The product from Part D is hydrogenated in glacial acetic acid (50 ml) over 10% palladium on carbon (approx. 0.2 g) at 40 p.s.i. overnight. The catalyst is filtered, washed with glacial acetic acid and the filtrate lyophilized. The resultant powder was redissolved in water and relyophilized (twice) to give the final product.

Similarly, using the appropriate acid chloride, the following additional compounds are prepared:

N-L-Aspartyl-N'-(2,2,5-trimethylcyclopentylcarbonyl) diamino acetic acid methyl ester.

N-L-Aspartyl-N'-(2,5-dimethylcyclopentylcarbonyl)-2,2-diamino acetic acid methyl ester.

N-L-Aspartyl-N'-fenchylcarbonyl-2,2-diamino acetic acid methyl ester.

N-L-Aspartyl-N'-dicyclopropylmethylcarbonyl-2,2-diamino acetic acid ester.

N-L-Aspartyl-N'-(2-t-butylcyclopentylcarbonyl)-2,2-diamino acetic acid methyl ester.

N-L-Aspartyl-N'-(1-t-butylcyclopropylmethylcarbonyl)-2,2-diamino acetic acid methyl ester.

N-L-Aspartyl-N'-(1-isopropyl-1-cyclopropylmethylcarbonyl)-2,2-diamino acetic acid methyl ester.

EXAMPLE 2

N-L-Aspartyl-N'-(2,2,5,5-tetramethylcyclopentylcarbonyl)-2,2-diaminopropionic acid methyl ester A. Sodium methoxide and methyl iodide are reacted with malonic acid dissolved in CH$_2$Cl$_2$ followed by the addition of an aqueous sodium hydroxide solution. The phases are separated and the aqueous phase is acidified with 1N HCl. The aqueous phase is extracted with methylene chloride, and the organic phase is collected and dried over MgSO$_4$.

Phosphorus and Bromine is added into dry 2-methylmalonic acid according to the procedure of Braun, in Berichte 42, p. 839 (1909) to form 2-Bromo-2-methyl malonic acid.

B. The above product is dissolved in ether, and liquid ammonia is added to the solution. After acidifying the solution with aqueous HCl, the two phases are separated and the organic phase is collected, washed with water and dried over anhydrous MgSO$_4$. The ether is evaporated to afford the 2-amino-2-methyl malonic acid.

The above product is esterified with methanol (1:1) and p-toluenesulfonic acid in CH$_2$Cl$_2$. Five percent sodium bicarbonate is added to the solution, and the organic phase and aqueous phases are separated and the aqueous phase collected. The aqueous phase is acidified with 1N HCl and extracted with methylene chloride and dried over MgSO$_4$. The methylene chloride is evaporated. Using preparative HPLC, the 2-amino-2-methylmalonic acid monomethyl ester is separated from organic impurities.

Using the procedure of Example 1 and substituting 2-amino-2-methylmalonic acid mono-methyl ester for 2-amino malonic acid monomethyl ester, the final product is prepared.

Similarly, by utilizing the appropriate acid chloride, the following compounds are prepared:

N-L-Aspartyl-N'-(2,2,5-trimethylcyclopentylcarbonyl)-2,2-diaminopropionic acid methyl ester.

N-L-Aspartyl-N'-(2,5-dimethylcyclopentylcarbonyl)-2,2-diaminopropionic acid methyl ester.

N-L-Aspartyl-N'-fenchylcarbonyl-2,2-diaminopropionic acid methyl ester.

N-L-Aspartyl-N'-dicyclopropylmethylcarbonyl)-2,2-diaminopropionic acid methyl ester.

N-L-Aspartyl-N'-(2-t-butylcyclopentylcarbonyl)-2,2-diaminopropionic acid methyl ester.

N-L-Aspartyl-N'-(1-t-butylcyclopropylmethylcarbonyl)-2,2-diaminopropionic acid methyl ester.

EXAMPLE 3
N-L-Aspartyl-N'-(2,2,5,5-tetramethylcyclopentylcarbonyl)-1,1-diamino cyclopropane The above compound is prepared according to the procedure of Example 1, except 1-amino-1-cyclopropane carboxylic acid is substituted for 2-aminomalonic mono-methyl ester.

In addition, the protecting group from the final product is removed by transfer hydrogenation, rather than catalytic hydrogenation. The N-(N'-Cbz-L-Aspartyl-beta-benzyl ester)-1,1-diaminocyclopropane, which is synthesized according to the above procedure, is dissolved in absolute ethanol at 0° C. in an ultrasound bath. Palladium on carbon (10%) is added. The hydrogen source, 1,4-cyclohexadiene, is added and ultrasound commenced for eight minutes. The slurry is then filtered through a bed of Celite with ethyl alcohol. Rotary evaporation affords the final product.

Similarly, using the appropriate acid chloride, the following additional compounds are prepared:

N-L-Aspartyl-N'-(2,2,5-trimethylcyclopentylcarbonyl)-1,1-diamino cyclopropane.

N-L-Aspartyl-N'-(2,5-dimethylcyclopentylcarbonyl)-1,1-diamino cyclopropane.

N-L-Asparytl-N'-fenchylcarbonyl-1,1-diamino cyclopropane.

N-L-Aspartyl-N'-dicyclopropylmethylcarbonyl-1,1-diamino cyclopropane.

N-L-Aspartyl-N'-(2-t-butylcyclopentylcarbonyl)-1,1-diamino cyclopropane.

N-L-Aspartyl-N'-(1-t-butylcyclopropylmethylcarbonyl)-1,1-diamino cyclopropane.

N-L-Aspartyl-N'-1-isopropyl-1-cyclopropylmethylcarbonyl)-1,1-diamino cyclopropane.

The compounds of this invention, possess greater stability than corresponding amides of the prior art. In addition, the present compounds lack a chiral center when A is other than a carbalkoxy group and are readily preparable and easily purified. The compounds wherein A is carbalkoxy, particularly carbomethoxy, are sweeter than corresponding amides of the prior art.

What is claimed is:

1. A compound represented by the formula:

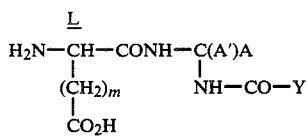

wherein

A is H, CO$_2$R where R is alkyl containing 1-3 carbon atoms;

A' is hydrogen or alkyl containing 1-3 carbon atoms;

Y is —(CHR$_2$)$_n$—R$_1$ or —CHR$_3$R$_4$;

R$_1$ is cycloalkyl, cycloakenyl, lower alkyl substituted cycloalkyl or cycloalkenyl, bicycloalkyl, bicycloalkenyl or tricycloalkyl containing up to 10 ring carbon atoms and up to a total of 12 carbon atoms;

R$_2$ is H or alkyl containing 1-4 carbon atoms;

R$_3$ and R$_4$ are each cycloalkyl containing 3-4 ring carbon atoms;

n=0 or 1; and m=0 or 1;

and food-acceptable salts thereof.

2. A compound according to claim 1 wherein R$_1$ is cyclopentylalkyl or cyclohexylalkyl containing a total of up to 10 carbon atoms.

3. A compound according to claim 1 wherein n=0.

4. A compound according to claim 1 wherein R$_1$ is mono-, di-, tri- or tetramethyl cycloalkyl or bicycloalkyl containing up to 10 carbon atoms.

5. A compound according to claim 4 wherein R$_1$ is a β-methyl-substituted cycloalkyl or bicycloalkyl.

6. A compound according to claim 4 wherein R$_1$ is a β,β or β,β'-dimethyl-substituted cycloalkyl or bicycloalkyl.

7. A compound according to claim 4 wherein R$_1$ is a β,β,β'trimethyl-substituted cycloalkyl or bicycloalkyl.

8. A compound according to claim 4 wherein R$_1$ is a β,β,β',β'-tetramethyl-substituted cycloalkyl or bicycloalkyl.

9. A compound according to claim 1 wherein R$_3$ and R$_4$ are cyclopropyl.

10. A compound represented by the formula:

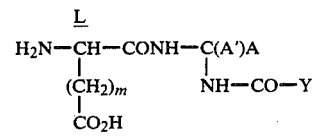

wherein

A is CO$_2$R wherein R is alkyl containing 1-3 carbon atoms;

A' is hydrogen;

Y is —(CHR$_2$)$_n$—R$_1$ or —CHR$_3$R$_4$;

R$_1$ is cycloalkyl, cycloalkenyl, lower alkyl substituted cycloalkyl or cycloalkenyl, bicycloalkyl, bicycloalkenyl or tricycloalkyl containing up to 10 ring carbon atoms and up to a total of 12 carbon atoms;

R$_2$ is H or alkyl containing 1-4 carbon atoms;

R$_3$ and R$_4$ are each cycloalkyk containing 3-4 ring carbon atoms;

n=0 or 1; and m=0 or 1;

and food-acceptable salts thereof.

11. A compound according to claim 10 wherein R$_1$ is cyclopentylalkyl or cyclohexylalkyl containing a total of up to 10 carbon atoms.

12. A compound according to claim 10 wherein n=0.

13. A compound according to claim 10 wherein R$_1$ is mono-, di-, tri or tetramethyl cycloalkyl or bicycloalkyl containing up to 10 carbon atoms.

14. A compound according to claim 13 wherein R$_1$ is a β-methyl-substituted cycloalkyl or bicycloalkyl.

15. A compound according to claim 13 wherein R$_1$ is a β,β or β,β'-dimethyl-substituted cycloalkyl or bicycloalkyl.

16. A compound according to claim 13 wherein $R_1$ is a $\beta,\beta,\beta'$-trimethyl-substituted cycloalkyl or bicycloalkyl.

17. A compound according to claim 13 wherein $R_1$ is a $\beta,\beta,\beta',\beta'$-tetramethyl-substituted cycloalkyl or bicycloalkyl.

18. A compound according to claim 10 wherein $R_3$ and $R_4$ are cyclopropyl.

19. A compound represented by the formula:

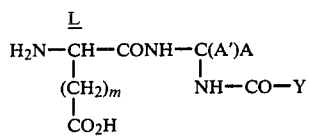

wherein
A is $CO_2R$, wherein R is alkyl containing 1–3 carbon atoms;
A' is alkyl containing 1–3 carbon atoms;
Y is $-(CHR_2)_n-R_1$ or $-CHR_3R_4$;
$R_1$ is cycloalkyl, cycloalkenyl, lower alkyl substituted cycloalkyl or cycloalkenyl, bicycloalkyl, bicycloalkenyl or tricycloalkyl containing up to 10 ring carbon atoms and up to a total of 12 carbon atoms;
$R_2$ is H or alkyl containing 1–4 carbon atoms;
$R_3$ and $R_4$ are each cycloalky containing 3–4 ring carbon atoms;
n=0 or 1;
m=0 or 1;
and food-acceptable salts thereof.

20. A compound according to claim 19 wherein $R_1$ is cyclopentylalkyl or cyclohexylalkyl containing a total of up to 10 carbon atoms.

21. A compound according to claim 20 wherein n=0.

22. A compound according to claim 19 wherein $R_1$ is mono-, di-, tri or tetramethyl cycloalkyl or bicycloalkyl containing up to 10 carbon atoms.

23. A compound according to claim 22 wherein $R_1$ is a $\beta$-methyl-substituted cycloalkyl or bicycloalkyl.

24. A compound according to claim 22 wherein $R_1$ is a $\beta,\beta$ or $\beta,\beta'$-dimethyl-substituted cycloalkyl or bicycloalkyl.

25. A compound according to claim 22 wherein $R_1$ is a $\beta,\beta,\beta'$-trimethyl-substituted cycloalkyl or bicycloalkyl.

26. A compound according to claim 22 wherein $R_1$ is a $\beta,\beta,\beta',\beta'$-tetramethyl-substituted cycloalkyl or bicycloalkyl.

27. A compound according to claim 19 wherein $R_3$ and $R_4$ are cyclopropyl.

28. A compound according to claim 1 which is N-L-Aspartyl-N'-(2,2,5,5-tetramethylcyclopentylcarbonyl)-2,2-diaminopropionic acid methyl ester.

29. A compound according to claim 1 which is N-L-Aspartyl-N'-(2,2,5-trimethylcyclopentylcarbonyl)-2,2-diaminopropionic acid methyl ester.

30. A compound according to claim 1 which is N-L-Aspartyl-N'-(2,5-dimethylcyclopentylcarbonyl)-2,2-diaminopropionic acid methyl ester.

31. A compound according to claim 1 which is N-L-Aspartyl-N'-(fenchylcarbonyl)-2,2-diaminopropionic acid methyl ester.

32. A compound according to claim 1 which is N-L-Aspartyl-N'-dicyclopropylmethylcarbonyl-2,2-diaminopropionic acid methyl ester.

33. A compound according to claim 1 which is N-L-Aspartyl-N'-(2-t-butylcyclopentylcarbonyl)-2,2-diaminopropionic acid methyl ester.

34. A compound according to claim 1 which is N-L-Aspartyl-N'-(1-t-butylcyclopropylmethylcarbonyl)-2,2-diaminopropionic acid methyl ester.

35. A compound according to claim 1 which is N-L-Aspartyl-N'-(2,2,5,5-tetramethylcyclopentylcarbonyl) 2,2-diamino acetic acid methyl ester.

36. A compound according to claim 1 which is N-L-Aspartyl-N'-(2,2,5-trimethylcyclopentylcarbonyl diamino acetic acid methyl ester.

37. A compound according to claim 1 which is N-L-Aspartyl-N'-(2,5-dimethylcyclopentylcarbonyl)-2,2-diamino acetic acid methyl ester.

38. A compound according to claim 1 which is N-L-Aspartyl-N'-fenchylcarbonyl-2,2-diamino acetic acid methyl ester.

39. A compound according to claim 1 which is N-L-Aspartyl-N'-dicyclopropylmethylcarbonyl-2,2-diamino acetic acid ester.

40. A compound according to claim 1 which is N-L-Aspartyl-N'-(2-t-butylcyclopentylcarbonyl)-2,2-diamino acetic acid methyl ester.

41. A compound according to claim 1 which is N-L-Aspartyl-N'-(1-t-butylcyclopropylmethylcarbonyl)-2,2-diamino acetic acid methyl ester.

42. A compound according to claim 1 which is N-L-Aspartyl-N'-(1-isopropyl-1-cyclopropylmethylcarbonyl)-2,2-diamino acetic acid methyl ester.

* * * * *